US012618235B1

(12) United States Patent (10) Patent No.: US 12,618,235 B1

Al Hamli (45) Date of Patent: May 5, 2026

(54) SANITIZING FLUID SPRAYER WITH LIGHT DISINFECTING

(71) Applicant: Mossab Al Hamli, Kuwait (KW)

(72) Inventor: Mossab Al Hamli, Kuwait (KW)

( * ) Notice: Subject to any disclaimer, the term of this patent is extended or adjusted under 35 U.S.C. 154(b) by 0 days.

(21) Appl. No.: 19/176,626

(22) Filed: Apr. 11, 2025

Related U.S. Application Data

(63) Continuation of application No. 19/034,344, filed on Jan. 22, 2025, now abandoned.

(51) Int. Cl.
| *E03D 9/00* | (2006.01) |
| *A61L 2/10* | (2026.01) |
| *A61L 2/24* | (2006.01) |

(52) U.S. Cl.
CPC .................. *E03D 9/00* (2013.01); *A61L 2/10* (2013.01); *A61L 2/24* (2013.01); *A61L 2202/11* (2013.01); *A61L 2202/121* (2013.01); *A61L 2202/14* (2013.01); *A61L 2202/17* (2013.01)

(58) Field of Classification Search
None
See application file for complete search history.

(56) References Cited

U.S. PATENT DOCUMENTS

| | | |
|---|---|---|
| 5,716,005 A | 2/1998 | McMahan |
| 5,987,659 A | 11/1999 | Cannizzaro |

| | | | |
|---|---|---|---|
| 5,991,937 A | 11/1999 | Safara | |
| 6,973,679 B1 * | 12/2005 | Schad ..................... E03D 9/085 4/443 |
| 6,978,492 B1 * | 12/2005 | Francisco .............. E03D 9/085 4/443 |
| 10,557,257 B1 * | 2/2020 | Al-Sabah ............... A47K 17/00 |
| 12,281,468 B2 * | 4/2025 | Garrels ..................... A61L 2/10 |
| 2006/0097189 A1 * | 5/2006 | Lim ..................... A47K 13/302 250/492.1 |
| 2019/0336629 A1 * | 11/2019 | Dobrinsky ............... A61L 2/10 |
| 2021/0164212 A1 * | 6/2021 | Baba ....................... A61L 2/084 |

* cited by examiner

*Primary Examiner* — Christine J Skubinna

(74) *Attorney, Agent, or Firm* — Nath, Goldberg & Meyer; Joshua B. Goldberg

(57) ABSTRACT

A sanitizing sprayer includes a fluid sprayer with a handle and flexible tubing connected to a water supply. A mount holds the fluid sprayer in a stowed position in which the fluid sprayer is surrounded by a sanitizing light source, such as an ultraviolet light source. The sanitizing light source may be automatically activated when the fluid sprayer is in the stowed position or when a door in connection with the mount is in a closed position. A timing circuit may automatically shut off the sanitizing light source after a set time period. The sanitizing sprayer may include a single cleaning fluid reservoir or a pair of cleaning fluid reservoirs mounted in sleeves of corresponding shape. Separate fluid conduits may be used to dispense cleaning fluid and water from the fluid sprayer. The fluid sprayer may include an incrementally adjustable dispensing valve for fixed pressure adjustments.

20 Claims, 7 Drawing Sheets

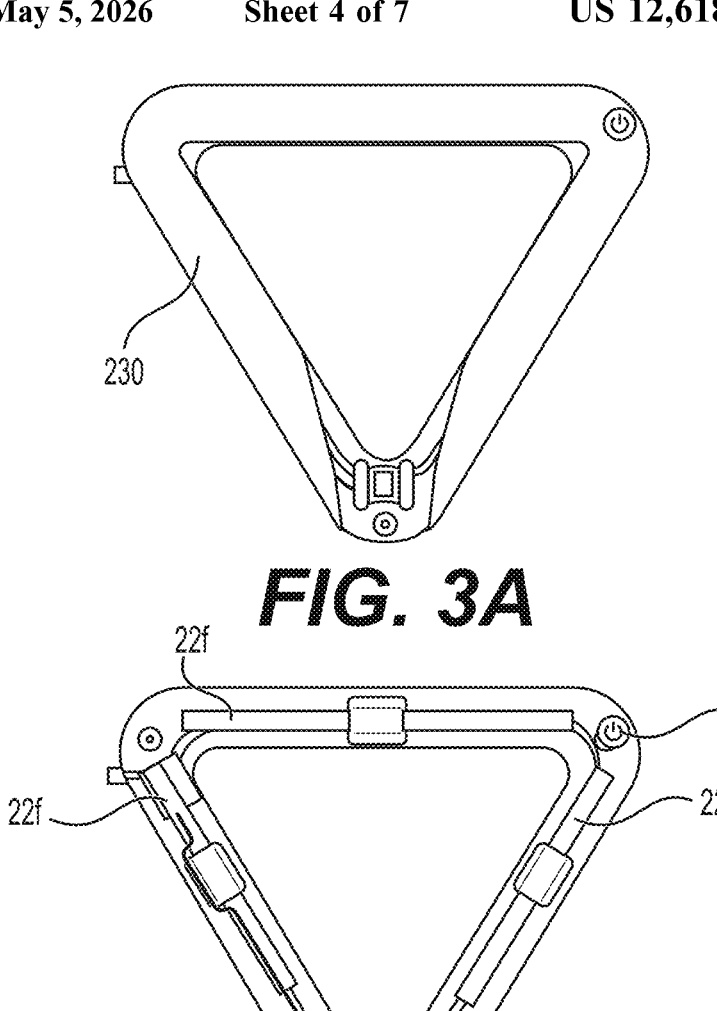
FIG. 3A
FIG. 3B
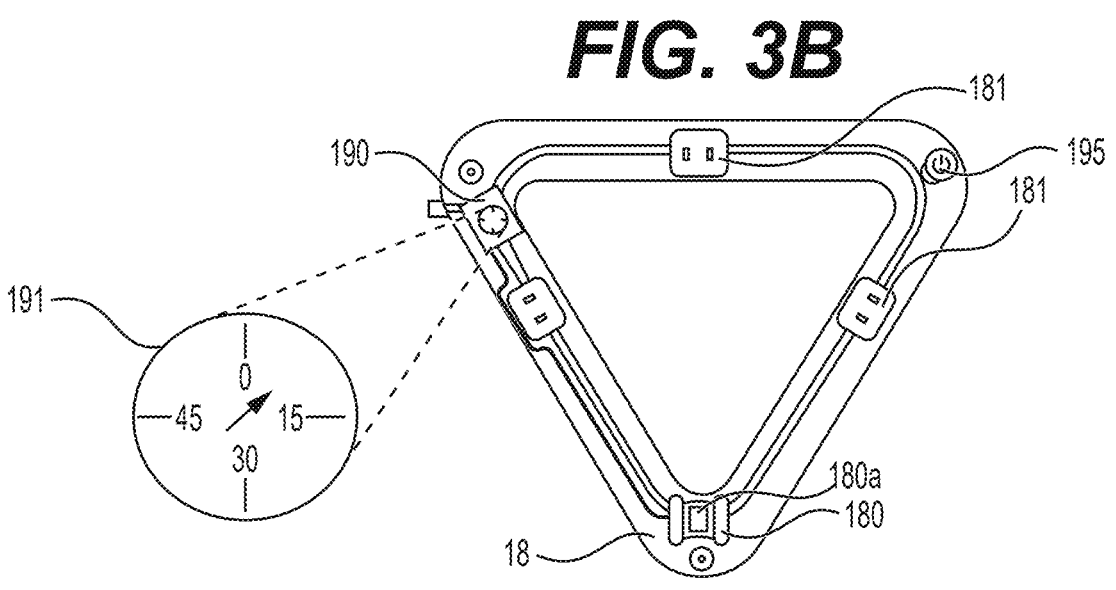
FIG. 3C

SANITIZING FLUID SPRAYER WITH LIGHT DISINFECTING

CROSS-REFERENCE TO RELATED APPLICATION

This application is a continuation of U.S. patent application Ser. No. 19/034,344, filed on Jan. 22, 2025, the entire contents of which are incorporated herein by reference.

BACKGROUND

Field

The disclosure of the present patent application relates to a personal hygiene sprayer known as a shataaf, and particularly to a personal hygiene sprayer including a disinfecting light source.

Description of Related Art

A personal hygiene sprayer, known as a shataaf (also spelled shattaf), is a handheld bidet or spray hose commonly used for personal hygiene in bathrooms, particularly in Middle Eastern and many South Asian countries. The shataaf serves as an alternative or compliment to toilet paper for cleansing purposes after using the toilet. In Middle Eastern countries, the use of water for cleansing after using the toilet is considered more hygienic and thorough than using toilet paper alone. The use of a shataaf also aligns with cultural and religious practices emphasizing cleanliness, such as those in Islam and the purity ritual known as Taharah.

A shortcoming of existing shataafs is the inability to dispense soap in addition to water and/or the inability to dispense different soaps of different fragrances. Another shortcoming is that despite its role in promoting cleanliness, the shataaf itself can become a source of contamination if not properly cleaned and maintained. The nozzle or spray head can come in contact with germs, particularly if it inadvertently touches the toilet or a user's body. Given that moist environments, such as bathrooms, are conducive to bacterial and fungal growth, care must be regularly taken to ensure the shataaf does not become unsanitary. Thus, new solutions are needed which provide consistent and reliable sanitizing of handheld shataaf sprayers solving the aforementioned problems.

SUMMARY OF THE INVENTION

A sanitizing sprayer is provided herein including a fluid sprayer with a handle and flexible tubing connecting the fluid sprayer to a water supply. A mount is provided to hold the fluid sprayer in a stowed position. An electrical power supply is connected to an sanitizing light source, such as an ultraviolet (UV) light source, the sanitizing light source is formed as a shape surrounding the fluid sprayer when the fluid sprayer is in the stowed position. The sanitizing light source may be formed as a polygon, a curvilinear shape, or a shape using a combination of straight and curvilinear lines. In a non-limiting embodiment, the sanitizing light source includes three sanitizing light bulbs arranged as a triangle.

The sanitizing light source may include any type of ultraviolet light capable of destroying bacterial microbes such as, but not limited to, UV-C light. The ultraviolet light source may be automatically activated when the fluid sprayer is in the stowed position. The mount for the fluid sprayer may include a clip having a switch that detects the presence of the fluid sprayer when the fluid sprayer is in the mounted position. In addition, the mount for the fluid sprayer may include a door configured to conceal the fluid sprayer and sanitizing light source when the fluid sprayer is in the stowed position and the door is in a closed position. Alternatively, the sanitizing light source may be automatically activated when the door is in the closed position.

The sanitizing sprayer may include a cleaning fluid reservoir. The fluid sprayer may be configured to dispense water from the water supply and cleaning fluid from the cleaning fluid reservoir. A pump may be in connection with the cleaning fluid reservoir to pump cleaning fluid to the fluid sprayer. The cleaning fluid reservoir may include an inclined base portion leading to a dispensing valve at a lowermost portion. The cleaning fluid reservoir may be mounted in a holding sleeve corresponding to the shape of the fluid cleaning reservoir. The holding sleeve may include a vertical cutout allowing visualization of the cleaning fluid reservoir beginning at a lowermost point of the cleaning fluid reservoir. A first fluid conduit may provide cleaning fluid from the cleaning fluid reservoir to the fluid sprayer, and a second fluid conduit may provide water from the water supply to the fluid sprayer.

In an embodiment, the sanitizing light source of the sanitizing sprayer may be formed in a plane parallel to a longitudinal axis of the fluid sprayer handle when the fluid sprayer is in a stowed position. The plane of the sanitizing light source may be coplanar and parallel to the longitudinal axis of the fluid sprayer. In another embodiment, the sanitizing light source may be formed in a plane perpendicular to a longitudinal axis of the fluid sprayer when the fluid sprayer is in the stowed position.

The fluid sprayer may include a dispensing valve configured to vary pressure of water dispensed from the fluid sprayer. The dispensing valve may be configured to be fixed in various incremental positions producing various incremental water dispensing pressures. In a non-limiting embodiment, the dispensing valve may include a hinged trigger that is fixed incrementally by a linearly sliding catch. In another embodiment, the fluid sprayer may be activated by a trigger, button, or other suitable type of dispensing valve allowing for water dispensing at different pressures.

In an embodiment, the sanitizing sprayer may include a pair of cleaning fluid reservoirs, wherein the fluid sprayer is configured to dispense water from the water supply and cleaning fluid from the cleaning fluid reservoirs. The cleaning fluid from the cleaning fluid reservoirs may be fed to the fluid sprayer from respective conduits of each cleaning fluid reservoir.

The sanitizing sprayer may include a timing switch connected to the sanitizing light source. The timing switch allows the sanitizing light source to be automatically activated for a predetermined amount of time. The predetermined amount of time may be fixed or may be adjusted by a user. A control means may be included for adjusting the amount of time the sanitizing light source is activated.

In an embodiment, a sanitizing sprayer is provided, including a fluid sprayer and a mounted configured to hold the fluid sprayer in a stowed position. Flexible tubing connects the fluid sprayer to a water supply from which the fluid sprayer is configured to dispense water. Multiple sanitizing light sources connected to a supply of electrical power surround the fluid sprayer when the fluid sprayer is in the stowed position. The multiple sanitizing light sources may be light emitting diode ultraviolet lights (LED-UV).

These and other features of the present subject matter will become readily apparent upon further review of the following specification.

BRIEF DESCRIPTION OF DRAWINGS

FIG. 3A is a front view of a cover of an ultraviolet light source.

FIG. 3B is a front view of an ultraviolet light source of three ultraviolet light bulbs forming a triangle.

FIG. 3C is a front view of electronic components on a mount for an ultraviolet light source.

Similar reference characters denote corresponding features consistently throughout the attached drawings.

DETAILED DESCRIPTION

Figure 1A:
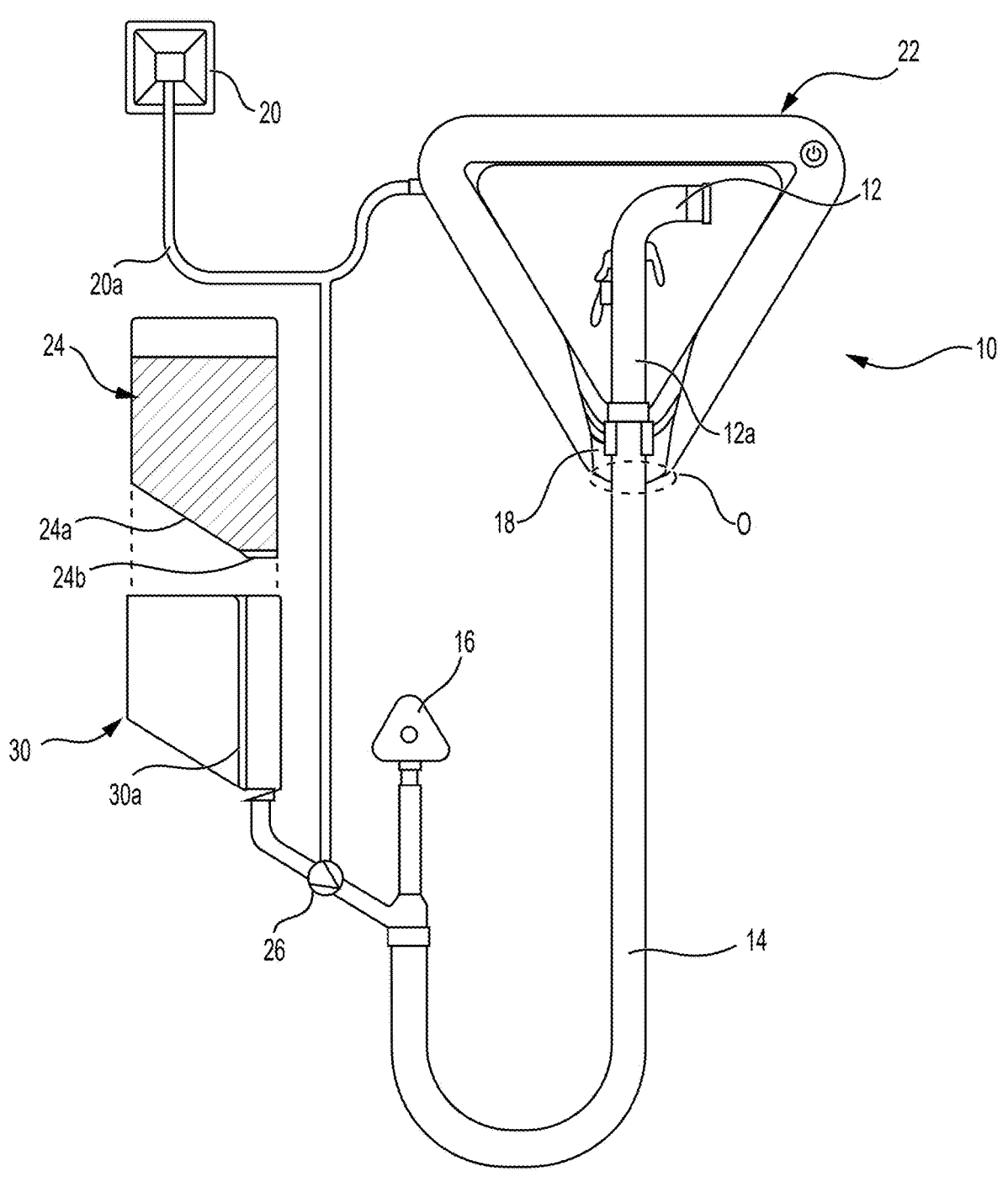
FIG. 1A is a front view of a sanitizing fluid sprayer with ultraviolet light disinfecting.
Figure 1B:
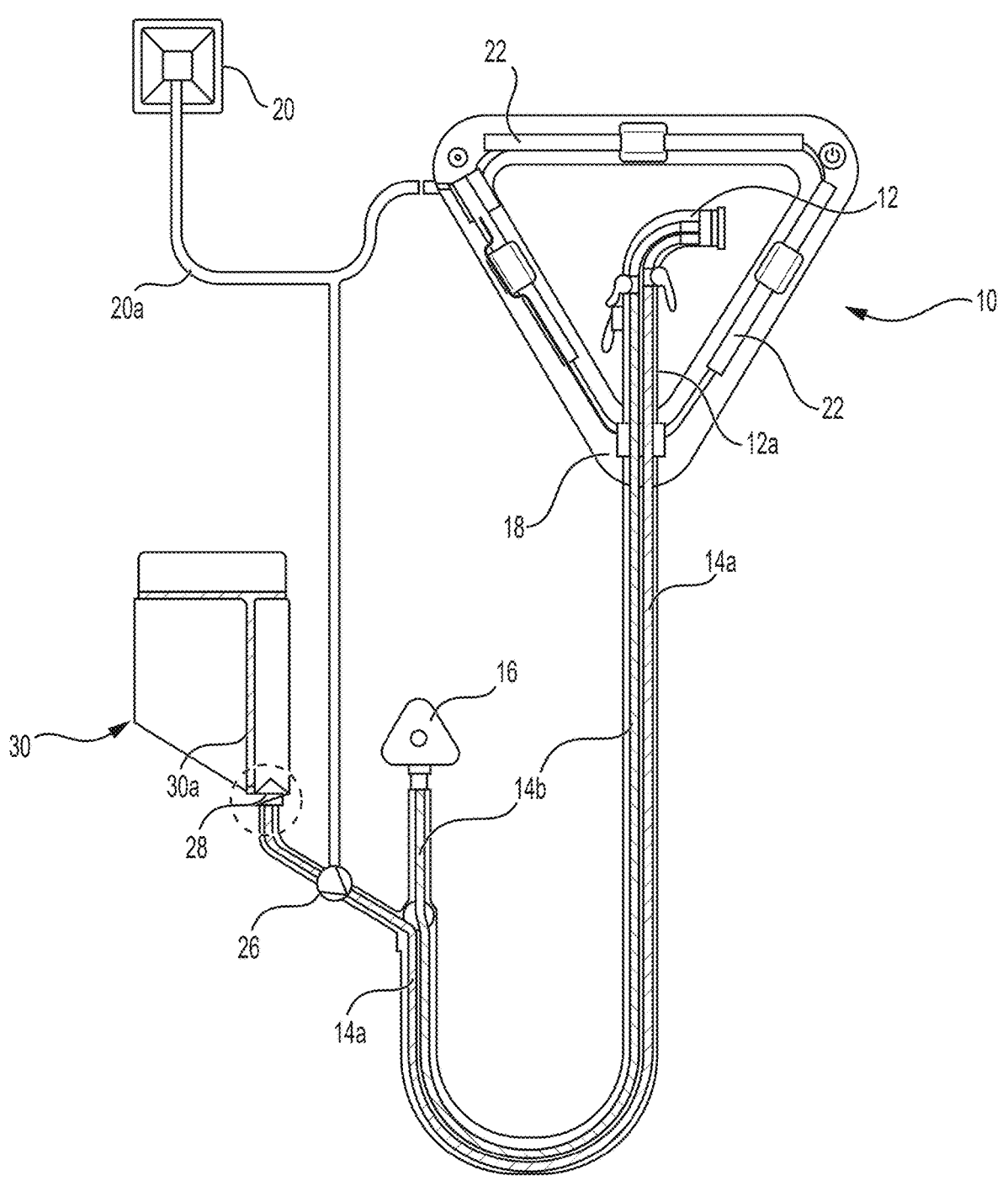
FIG. 1B is a front partial cutout view of a sanitizing fluid sprayer with ultraviolet light disinfecting.

Referring to FIGS. 1A-B, a sanitizing sprayer 10, also known as a shataaf, is provided including a fluid sprayer 12, with handle 12a for handheld manipulation and flexible tubing 14 connecting the fluid sprayer 12 to a water supply 16 such as a water supply line or water tank of a residential or commercial building. A mount 18 is provided to hold the fluid sprayer 12 in a stowed position as shown. An electrical power supply 20 is connected via wiring 20a to an sanitizing light source 22 providing disinfecting light directed at the fluid sprayer 12. In a non-limiting embodiment, sanitizing light source is an ultraviolet (UV) light source, but could potentially include other types of sanitizing light. As is known, the electrical power supply 22 may include any suitable source of electrical power including an AC power supply, DC power supply, solar power, and generator power. The sanitizing light source 22 is formed as a shape surrounding the fluid sprayer 12 when the fluid sprayer is in the stowed position. In the non-limiting embodiment of FIGS. 1A-B, the sanitizing light source 22 is formed as a polygon, and specifically a triangle, surrounding the fluid sprayer 12.

As used herein, when describing the shape of the sanitizing light source, the terms "surrounding the fluid sprayer" are to be interpreted as "effectively surrounding" or "substantially surrounding" the fluid sprayer 12 with the exception of a small opening O through which the handle 12a and/or flexible tubing 14 extends.

The sanitizing sprayer may include a cleaning fluid reservoir 24. The fluid sprayer 12 may be configured to dispense water from the water supply 16 and cleaning fluid from the cleaning fluid reservoir 24. A pump 26 of any suitable kind may be in connection with the cleaning fluid reservoir 24 to pump cleaning fluid to the fluid sprayer 12. The pump 26 may be, for example, a peristaltic pump powered electronically, but in other embodiments could be incorporated in the handle 12a as a manual trigger pump of the well-known type used on bottle sprayers and the like.

The cleaning fluid reservoir 24 may include an inclined base portion 24a leading to a dispensing valve 28 (See FIG. 1B) at a lowermost portion 24b (See FIG. 1A). The cleaning fluid reservoir 24 may be mounted in a holding sleeve 30 corresponding to the shape of the cleaning fluid reservoir 24. FIG. 1A depicts cleaning fluid reservoir 24 being inserted into holding sleeve 30. The holding sleeve 30 may include a vertical cutout 30a allowing visualization of the cleaning fluid reservoir 24 beginning at a lowermost point 24b of the cleaning fluid reservoir 24. A first fluid conduit 14a shown in FIG. 1B may provide cleaning fluid from the cleaning fluid reservoir 24 to the fluid sprayer 12, and a second fluid conduit 14b may provide pressurized water from the water supply 16 to the fluid sprayer 12. The water and cleaning fluid may be simultaneously dispensed, but are more preferably dispensed through individual valves, to be explained below in reference to FIG. 5.

Figure 2C:
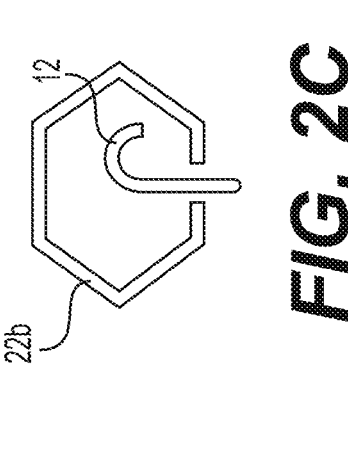
FIG. 2C is an illustration of a sanitizing fluid sprayer surrounded by a hexagon shape ultraviolet light source.
Figure 2G:
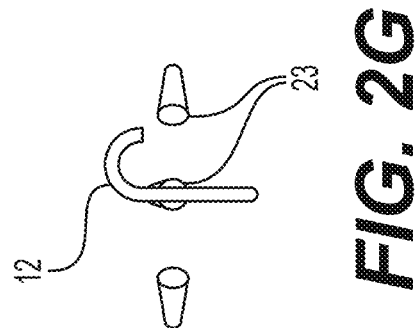
FIG. 2G is an illustration of a sanitizing fluid sprayer surrounded by multiple sanitizing light sources.
Figure 2B:
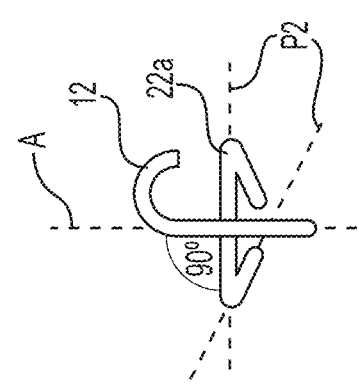
FIG. 2B is an illustration of a sanitizing fluid sprayer surrounded by a triangle shape ultraviolet light source in a plane perpendicular to the longitudinal axis of the fluid sprayer.
Figure 2F:
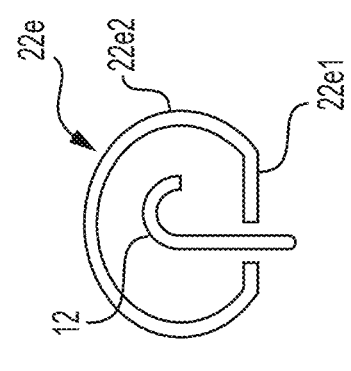
FIG. 2F is an illustration of a sanitizing fluid sprayer surrounded by an ultraviolet light source in a shape of straight and curvilinear lines.
Figure 2A:
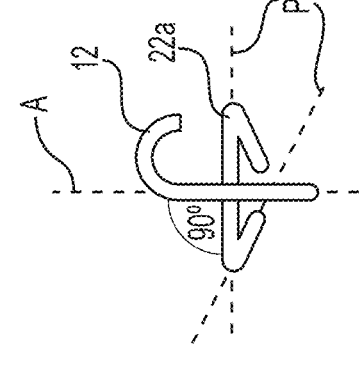
FIG. 2A is an illustration of a sanitizing fluid sprayer surrounded by a triangle shape ultraviolet light source in a plane parallel to the longitudinal axis of the fluid sprayer.
Figure 2E:
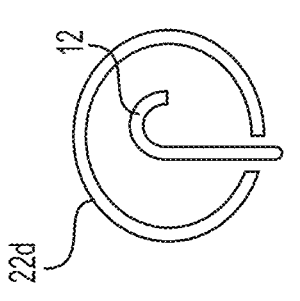
FIG. 2E is an illustration of a sanitizing fluid sprayer surrounded by a circle shape ultraviolet light source.
Figure 2D:
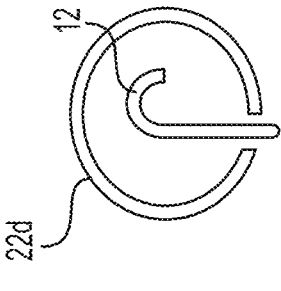
FIG. 2D is an illustration of a sanitizing fluid sprayer surrounded by a square shape ultraviolet light source.

Turning to FIGS. 2A-G, the sanitizing light source 22 may be formed as a polygon such as a triangle 22a as shown in FIGS. 2A-B, a hexagon 22b as shown in FIG. 2C, square 22c as shown in FIG. 2D, or any other polygonal shape. Alternatively, sanitizing light source 22 may be formed as a curvilinear shape such as a circle 22d shown in FIG. 2E, or a shape 22e using a combination of straight lines 22e1 and curvilinear lines 22e2 as shown in FIG. 2F. In a non-limiting embodiment, the sanitizing light source 22 may be formed in a plane P1 that is parallel to a longitudinal axis A of the fluid sprayer 12, as shown in FIG. 2A. Plane P1 may be parallel and coplanar with longitudinal axis A. Alternatively, as shown in FIG. 2B, the sanitizing light source 22a may be formed in a plane P2 that is perpendicular to the longitudinal axis A of fluid sprayer 12. For example, in a situation where fluid sprayer 12 is mounted within a cutout formed in a wall, it may be desirable to position the sanitizing light source within a plane P2 that is perpendicular to the longitudinal axis A of the fluid sprayer 12. In another embodiment, the ultraviolet light source may be formed in a plane (not shown) that is oblique to the longitudinal axis of the fluid sprayer.

In another embodiment, shown in FIG. 2G, multiple sanitizing light sources 23 may be positioned surrounding the fluid sprayer 12, when fluid sprayer 12 is in the stowed position. Light sources 23 may be, for example, light emitting diode ultraviolet lights. However, other light sources may potentially be used such as blue light, xenon light, infrared, an ultraviolet light source, or any other light source capable of providing sanitizing light.

Figure 3D:
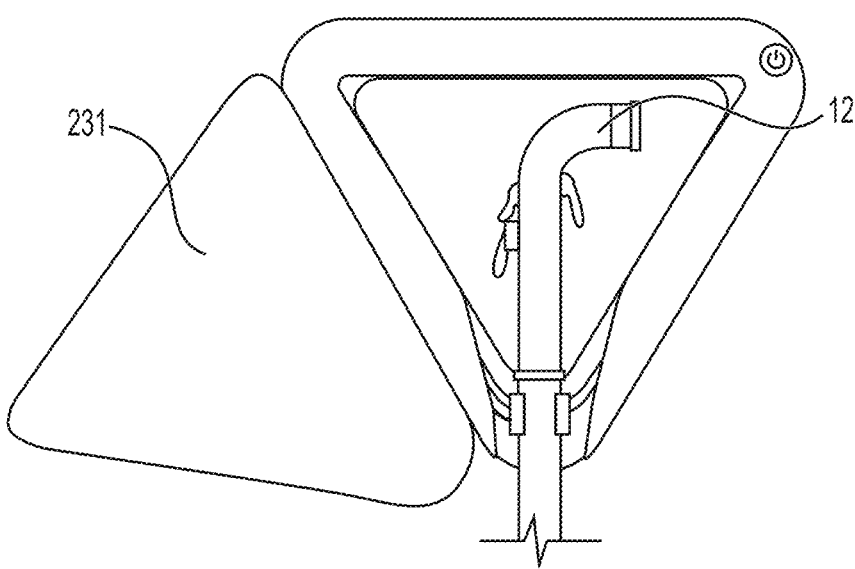
FIG. 3D is a front view of a fluid sprayer in a stowed position on a mount having a door in an open position.

Referring now to FIGS. 3A-E, additional details of the sanitizing light source are shown. As shown in FIG. 3A, a cover 230 may be included corresponding to the shape of the sanitizing light source, which, in the non-limiting embodiment of FIG. 3B, is three sanitizing light bulbs 22f arranged as a triangle. Although the embodiment of FIG. 3B shows three separate bulbs 22f arranged as a triangle, it is conceivable that a single bulb shaped as a triangle or any other possible shape such as those of FIGS. 2A-F may be used as the ultraviolet light source. Likewise, multiple bulbs may be used and arranged in a shape surrounding the fluid sprayer as the sanitizing light source and provide sanitizing light directed at the fluid sprayer, as in the embodiment of FIG. 3B.

The sanitizing light source may include any type of ultraviolet light capable of destroying bacterial microbes such as, but not limited to, UV-C light which has a wavelength of 200-280 nm and is highly effective in killing bacteria, viruses and fungi. The ultraviolet light source may be automatically activated when the fluid sprayer is in the stowed position. The mount 18 for the fluid sprayer may include a clip 180 having a switch 180a connected thereto that detects the presence of the fluid sprayer 12 when the fluid sprayer 12 is in the stowed or mounted position. Sockets 181 are included for receiving the sanitizing light bulbs 22f of FIG. 3B. A timing switch 190 may be included and allow the sanitizing light source 22f to be automatically activated for a set amount of time, for example 5 minutes, 15 minutes, 30 minutes, etc. The set amount of time may be fixed or may be adjustable by a user. A control means 191 may be included, such as the rotary switch shown, as an example but also a digital control, etc., for adjusting the amount of time the sanitizing light source is activated. In addition, an on/off power button switch 195 may be included for manually turning on or off the sanitizing light source.

Figure 3E:
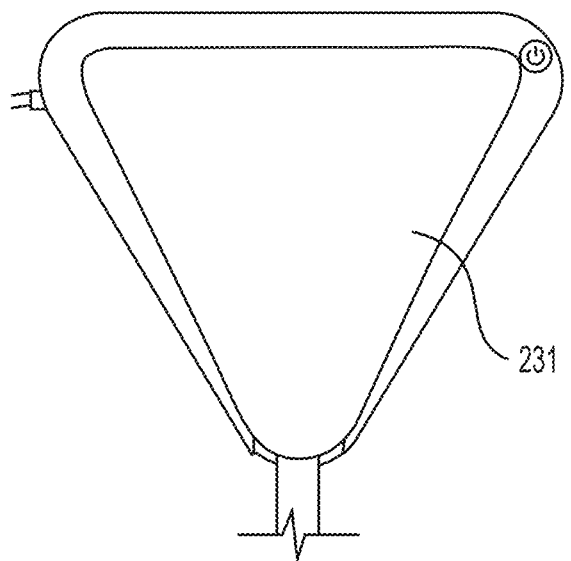
FIG. 3E is a front view of a fluid sprayer in a stowed position on a mount having a door in a closed position.

In addition, a door 231 may be included as shown in FIG. 3D that is configured to conceal the fluid sprayer 12 and sanitizing light source when the fluid sprayer 12 is in the stowed position and the door 231 is in a closed position of FIG. 3E. The sanitizing light source may be automatically activated by a switch (not shown) when the door 231 is in the closed position.

Figure 4:
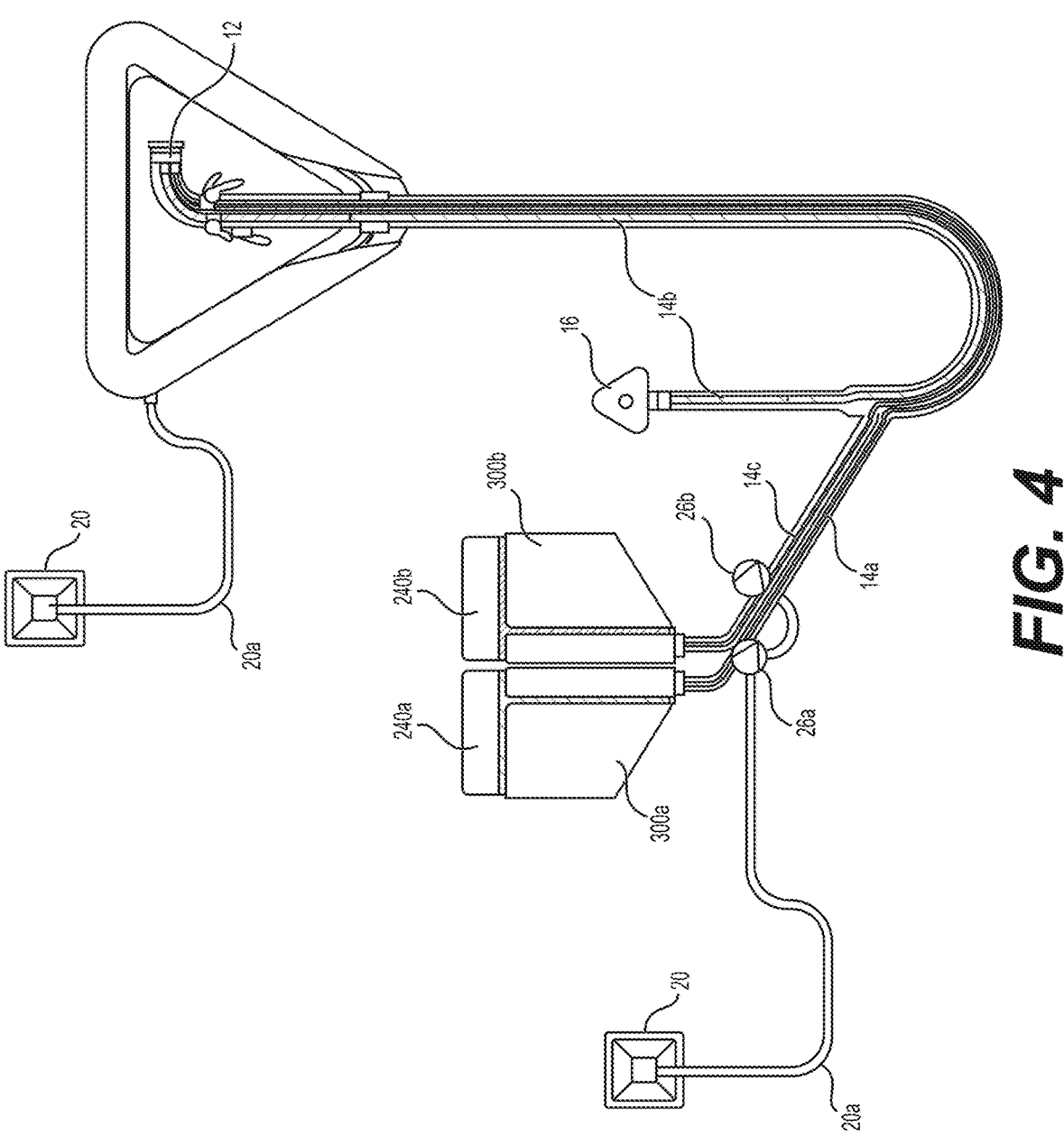
FIG. 4 is a front partial cutout view of a sanitizing fluid sprayer using two cleaning fluid reservoirs.

Referring now to FIG. 4, in an embodiment, the sanitizing sprayer may include a pair of cleaning fluid reservoirs 240a, 240b contained in respective holding sleeves 300a, 300b, wherein the fluid sprayer 12 is configured to dispense water from the water supply 16 and cleaning fluid from the cleaning fluid reservoirs 240a, 240b. The cleaning fluid from the cleaning fluid reservoirs may be fed to the fluid sprayer 12 from respective conduits 14a, 14c of each cleaning fluid reservoir 240a, 240b. Respective pumps 26a, 26b may be included to pump cleaning fluid from cleaning fluid reservoirs 240a, 240b. The dual cleaning fluid reservoirs 240, 240b allow, for example, the use of different fragrances of cleaning fluid, such as "him" and "her" fragrances.

Figure 5:
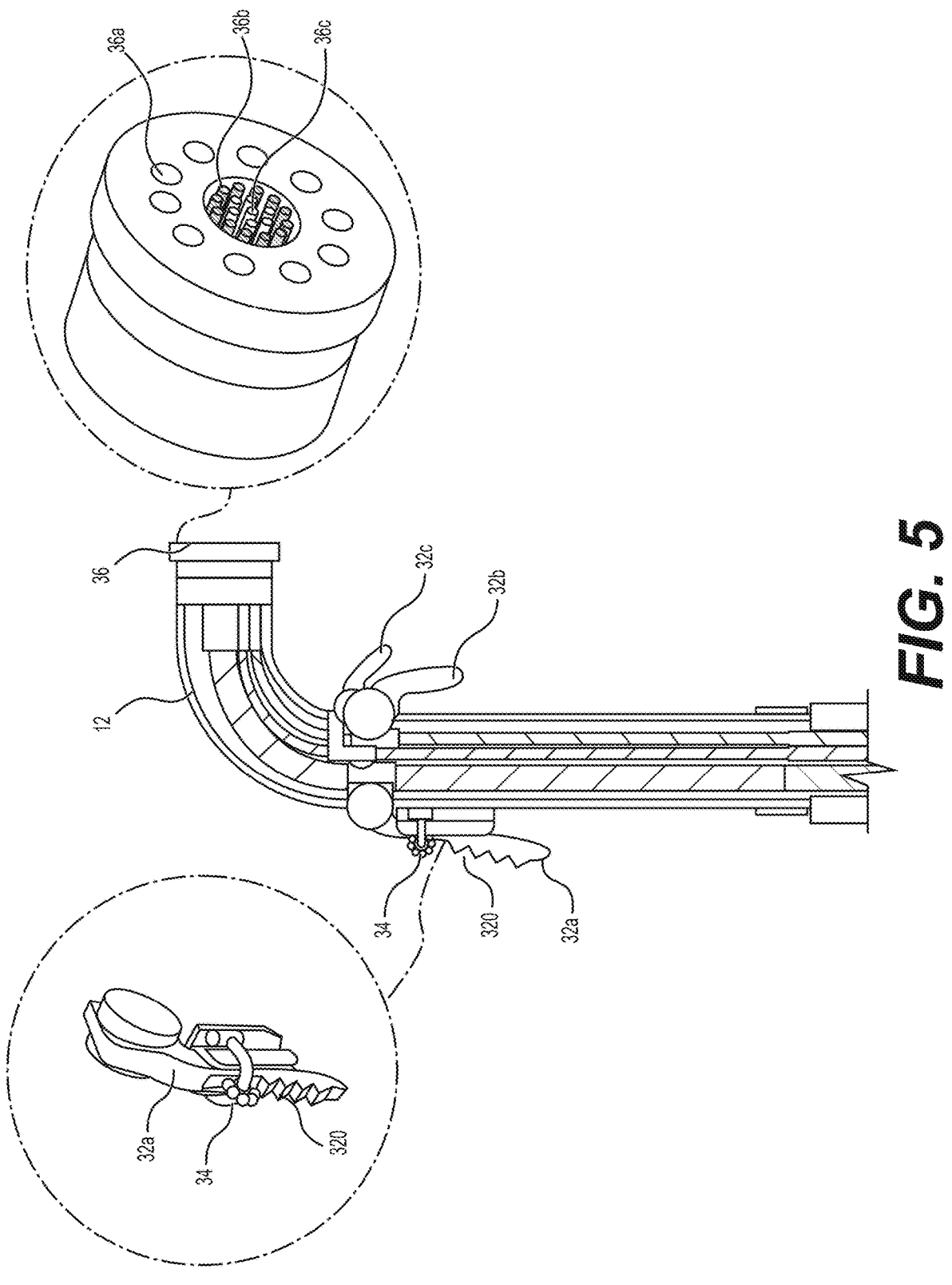
FIG. 5 provides a front cutout view and perspective close up views of dispensing valves and nozzles of a fluid sprayer.

Referring now to FIG. 5, the fluid sprayer may include a dispensing valve 32a configured to vary pressure of water dispensed from the fluid sprayer 12. The dispensing valve 32a may be fixed in various incremental positions 320 producing various incremental water dispensing pressures. In a non-limiting embodiment, the dispensing valve 32a may include a hinged trigger as shown that is fixed incrementally by a linearly sliding catch 34. In another embodiment, the fluid sprayer may be activated by a button, and/or other suitable type of dispensing valve allowing for water dispensing at different pressures. Similar dispensing valves 32b, 32c may be included for dispensing cleaning fluid from the respective first and second cleaning fluid reservoirs. Alternatively, dispensing valves 32b, 32c could be provided as manual trigger pumps for the dispensing of cleaning fluid. A dispensing nozzle 36 of fluid sprayer 12 may include separate orifices 36a-c for respective dispensing of water 36a, first cleaning fluid 36b, and second cleaning fluid 36c.

It is to be understood that the sanitizing fluid sprayer with ultraviolet light disinfecting is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A sanitizing sprayer, comprising:
   a handheld fluid sprayer;
   flexible tubing connecting the handheld fluid sprayer to a water supply;
   a mount configured to hold the handheld fluid sprayer in a stowed position;
   a power supply; and
   a sanitizing light source connected to the power supply, wherein the sanitizing light source is configured to sanitize the handheld fluid sprayer and is formed as a shape surrounding the handheld fluid sprayer when the handheld fluid sprayer is in the stowed position,
   wherein the sanitizing light source includes an opening through which at least one selected from a handle of the handheld fluid sprayer and the flexible tubing extends when the handheld fluid sprayer is in the stowed position.

2. The sanitizing sprayer of claim 1, wherein the sanitizing light source is formed as a polygon surrounding the handheld fluid sprayer in the stowed position.

3. The sanitizing sprayer of claim 2, wherein the sanitizing light source is formed as a triangle surrounding the handheld fluid sprayer in the stowed position.

4. The sanitizing sprayer of claim 3, wherein the sanitizing light source comprises three sanitizing light bulbs formed as the triangle surrounding the handheld fluid sprayer in the stowed position.

5. The sanitizing sprayer of claim 1, wherein the sanitizing light source is configured as a curvilinear shape surrounding the handheld fluid sprayer in the stowed position.

6. The sanitizing sprayer of claim 1, wherein the sanitizing light source is configured to be automatically activated by a switch when the handheld fluid sprayer is in the stowed position.

7. The sanitizing sprayer of claim 1, further comprising a door attached to the mount, wherein the door is configured to conceal the handheld fluid sprayer and to conceal the sanitizing light source when the handheld fluid sprayer is in the stowed position and the door is in a closed position.

8. The sanitizing sprayer of claim 7, wherein the sanitizing light source is configured to automatically activate when the door is in the closed position.

9. The sanitizing sprayer of claim 1, further comprising a cleaning fluid reservoir, wherein the handheld fluid sprayer is configured to dispense water from the water supply and cleaning fluid from the cleaning fluid reservoir.

10. The sanitizing sprayer of claim 1, wherein the handheld fluid sprayer comprises a handle and wherein the shape of the sanitizing light source surrounding the handheld fluid sprayer in the stowed position is formed entirely in a plane parallel to a longitudinal axis of the handle when the handheld fluid sprayer is in the stowed position.

11. The sanitizing sprayer of claim 1, wherein the handheld fluid sprayer includes a dispensing valve configured to vary pressure of water dispensed from the handheld fluid sprayer.

12. The sanitizing sprayer of claim 11, wherein the dispensing valve is configured to be fixed in various incremental positions producing various incremental water dispensing pressures.

13. The sanitizing sprayer of claim 1, further comprising a pair of cleaning fluid reservoirs, wherein the handheld fluid sprayer is configured to dispense water from the water supply and cleaning fluid from the cleaning fluid reservoirs.

14. The sanitizing sprayer of claim 1, further comprising a timing switch connected to the sanitizing light source, wherein the timing switch allows the sanitizing light source to be automatically activated for a set amount of time.

15. The sanitizing sprayer of claim 14, further comprising control means for adjusting the set amount of time.

16. A sanitizing sprayer, comprising:

a handheld fluid sprayer;

a mount selectively connectable to the handheld fluid sprayer such that the handheld fluid sprayer can be selectively held by the mount in a stowed position and selectively disconnected from the mount;

flexible tubing connecting the handheld fluid sprayer to a water supply, wherein the handheld fluid sprayer is configured to dispense water from the water supply;

multiple sanitizing light sources connected to a supply of electrical power, wherein the multiple sanitizing light sources are configured to sanitize the handheld fluid sprayer and surround the handheld fluid sprayer when the handheld fluid sprayer is selectively connected to the mount in the stowed position; and a door attached to the mount, wherein the door is configured to conceal the handheld fluid sprayer and to conceal the multiple sanitizing light sources when the handheld fluid sprayer is selectively connected to the mount in the stowed position and the door is in a closed position.

17. The sanitizing sprayer of claim 16, wherein the multiple sanitizing light sources are light emitting diode ultraviolet (LED-UV) lights.

18. The sanitizing sprayer of claim 17, further comprising a timing switch connected to the multiple sanitizing light sources, wherein the timing switch allows the multiple sanitizing light sources to be automatically activated for a set amount of time.

19. A sanitizing sprayer, comprising:

a handheld fluid sprayer comprising a handle;

flexible tubing connecting the handheld fluid sprayer to a water supply;

a mount configured to hold the handheld fluid sprayer in a stowed position;

a power supply; and a sanitizing light source connected to the power supply, wherein the sanitizing light source surrounds the handle of the handheld fluid sprayer when the handheld fluid sprayer is in the stowed position, wherein the sanitizing light source is configured to sanitize the handle of the handheld fluid sprayer.

20. The sanitizing sprayer of claim 19, wherein the sanitizing light source is formed entirely in a plane that is coplanar with a longitudinal axis of the handle when the handheld fluid sprayer is in the stowed position.

* * * * *